(12) United States Patent
Stern et al.

(10) Patent No.: US 11,859,194 B2
(45) Date of Patent: Jan. 2, 2024

(54) COMPOSITIONS AND METHODS USEFUL FOR THE REGULATION OF ABIOTIC STRESS RESPONSES IN HIGHER PLANTS

(71) Applicant: Boyce Thompson Institute for Plant Research, Inc., Ithaca, NY (US)

(72) Inventors: David Stern, Burdett, NY (US); Coralie Evelyn Salesse-Smith, Newfield, NY (US); Leila Feiz, Ithaca, NY (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 15/371,185

(22) Filed: Dec. 6, 2016

(65) Prior Publication Data

US 2017/0081678 A1    Mar. 23, 2017

Related U.S. Application Data

(63) Continuation-in-part of application No. PCT/US2015/034430, filed on Jun. 5, 2015.

(60) Provisional application No. 62/008,913, filed on Jun. 6, 2014.

(51) Int. Cl.
    *C12N 15/82*    (2006.01)
    *C07K 14/415*    (2006.01)
    *C12N 9/88*    (2006.01)

(52) U.S. Cl.
    CPC ........ *C12N 15/8271* (2013.01); *C07K 14/415* (2013.01); *C12N 9/88* (2013.01); *C12N 15/8251* (2013.01); *C12N 15/8261* (2013.01); *C12N 15/8269* (2013.01); *C12N 15/8273* (2013.01); *C12Y 207/00* (2013.01); *C12Y 401/01039* (2013.01)

(58) Field of Classification Search
None
See application file for complete search history.

(56) References Cited

U.S. PATENT DOCUMENTS

2010/0299782 A1    11/2010    Schroeder et al.

OTHER PUBLICATIONS

Anderson and Backlund, 2008, Plant Physiology and Biochemistry 46: 275-291.*
Feiz et al., 2012, The Plant Cell 24: 3435-3446, with supplemental data.*
Zea mays Rubisco accumulation factor 1, chloroplastic (RAF1) sequence, GenBank accession No. NM_001147291.1, published Oct. 21, 2018.*
Parry et al., 2013, Journal of Experimental Botany 64: 717-730.*
Suzuki and Makino, 2012, Plant Physiology 160: 533-540.*
Christensen and Quail, 1996, Ubiquitin promoter-based vectors for high-level expression of selectable and/or screenable marker genes in monocotyledonous plants, Transgenic Research 5: 213-218.*
Brutnell, Thomas P. et al., "Bundle Sheath Defective2, a Novel Protein Required for Post-Translational Regulation of the rbcL Gene of Maize", The Plant Cell, 11: 849-864 (1999).
Feiz, Leila et al., "Ribulose-1,5-Bis-Phosphate Carboxylase/Oxygenase Accumulation Factor 1 is Required for Holoenzyme Assembly in Maize", The Plant Cell, 24: 3435-3446 (2012).
Long, S.P. et al., "C4 photosynthesis at low temperatures", Plant, Cell & Environment, 6(4): 345-363 (1983) [Abstract only].
Naidu, Shawna L. et al., "Potential mechanisms of low-temperature tolerance of C4 photosynthesis in Miscanthus X giganteus: an in vivo analysis", Planta, 220: 145-155 (2004).
Naidu, Shawna L. et al., "Cold Tolerance of C4 photosynthesis in Miscanthus X giganteus: Adaptation in Amounts and Sequence of C4 Photosynthetic Enzymes", Plant Physiology, 132: 1688-1697 (2003).
Spence, Ashley K. et al., "Understanding the Physiological and Molecular Basis of Chilling Tolerance Across Species of the C4 Genera Miscanthus and Spartina", Dissertation, University of Illinois at Urbana-Champaign,, pp. 1-146 (2012).
Suzuki, Yuji et al., "Increased Rubisco Content in Transgenic Rice Transformed with the "Sense" rbcS Gene", Plant Cell Physiol., 48(4): 626-637 (2007).
Wang, Dafu et al., "Cool C4 Photosynthesis: Pyruvate Pi Dikinase Expression and Activity Corresponds to the Exceptioknal Cold Tolerance of Carbon Assimilation in Miscanthus X giganteus", Plant Physiology, 148: 557-567 (2008).
Whitney, Spencer M. et al., "Improving recombinant Rubisco biogenesis, plant photosynthesis and growth by coexpressing its ancillary RAF1 chaperone", PNAS, 112(11): 3564-3569 (2015).
Wostrikoff, Katia et al., "Rubisco large-subunit translation is autoregulated in response to its assembly state in tobacco chloroplasts", PNAS: 104 (15): 6466-6471 (2007).
Yamori, Wataru et al., "Rubisco activase is a key regulator of non-steady-state photosynthesis at any leaf temperature and, to a lesser extent, of steady-state photosynthesis at high temperature", The Plant Journal, 71:p. 871-880 (2012).
NCBI_NP_001140763, hypothetical protein [Zea mays], Accession: NP_001140763, Dec. 13, 2013 [online].
International Search Report/Written Opinion, dated Aug. 21, 2015, issued in corresponding International Application No. PCT/US2015/34430.

* cited by examiner

*Primary Examiner* — Vinod Kumar
(74) *Attorney, Agent, or Firm* — Kathleen D. Rigaut; Howson & Howson LLP

(57) ABSTRACT

Compositions and methods for creating plants exhibiting enhanced resistance to abiotic stresses, especially cold stress are disclosed.

6 Claims, 10 Drawing Sheets

* p<0.05

COMPOSITIONS AND METHODS USEFUL FOR THE REGULATION OF ABIOTIC STRESS RESPONSES IN HIGHER PLANTS

This application claims priority to PCT/US2015/034430 filed Jun. 5, 2015 which in turn claims priority to U.S. Provisional Application No. 62/008,913 filed Jun. 6, 2014, the entire disclosure being incorporated herein by reference as though set forth in full.

FIELD OF THE INVENTION

This invention relates to the fields of genetic engineering and transgenic plants. More specifically the invention provides compositions and methods for regulating ribulose bisphosphate carboxylase/oxygenase assembly and accumulation in higher plants, thereby altering abiotic stress responses and increasing photosynthetic activity in said plant.

BACKGROUND OF THE INVENTION

Several publications and patent documents are cited throughout the specification in order to describe the state of the art to which this invention pertains. Each of these citations is incorporated herein by reference as though set forth in full.

Ribulose 1,5-bisphosphate carboxylase/oxygenase (Rubisco) is the major enzyme by which green plants, algae, cyanobacteria and other autotrophic organisms sequester carbon dioxide into organic compounds via the Calvin-Benson pathway (Andersson and Backlund, 2008). Rubisco catalyzes the photosynthetic carbon reduction and the photorespiratory carbon oxidation reactions of the substrate ribulose-1,5-bisphosphate (RuBP) with $CO_2$ and $O_2$, respectively. The inefficiency of Rubisco in fixing $CO_2$ has a limiting impact on agricultural productivity and in compensation, Rubisco accounts for as much as 20-30% and 4-9% of total nitrogen compounds in $C_3$ and $C_4$ higher plants, respectively (Feller et al., 2008).

Attempts to improve the catalytic properties of higher plant Rubisco (reviewed in Parry et al., 2003; Mueller-Cajar and Whitney, 2008B) have met with only modest success, which can be traced in part to the lack of a comprehensive knowledge of its biogenesis and the absence of an in vitro reconstitution system. Form I Rubisco, found in higher plants, algae and cyanobacteria, is a hexadecamer composed of eight large (50-kDa) and eight small (13-15 kDa) subunits, denoted here as LS and SS, respectively. The genes encoding LS (rbcL) and SS (RBCS) are located in the chloroplast and nuclear genomes, respectively. SS is expressed as a pre-protein that is translocated into the chloroplast, where its signal peptide is cleaved prior to its assembly with LS (Nishimura et al., 2008). The two subunits accumulate stoichiometrically in the chloroplast, a phenomenon which is mediated by feedback inhibition of LS synthesis by unassembled subunits (Rodermel et al., 1996; Wostrikoff and Stern, 2007), as well as proteolysis of unassembled SS (Kanevski and Maliga, 1994).

Attempts to delineate the assembly pathway of Form I Rubisco have exploited two major approaches; in vivo assembly of cyanobacterial Rubisco mainly using *E. coli* cells, and in vitro reconstitution of the enzyme via addition of individual components. In the first approach, assembly of *Synechococcus* PCC 6301 Rubisco in *E. coli* resulted in a functional enzyme (van der Vies et al., 1986; Tabita, 1999). LS was also expressed alone in this way, and shown to have minimal catalytic activity in the octamer form, which could be enhanced by the subsequent addition of SS (Andrews, 1988).

Rubisco assembly requires multiple chaperones. The probable role of chaperonin (Cpn) 60 was first discovered through the co-purification of chloroplast Rubisco with a protein homologous to *E. coli* GroEL (Barraclough and Ellis, 1980). It was subsequently demonstrated that overexpression of *E. coli* GroEL-ES significantly promoted the assembly and activity of *Synechococcus* Rubisco in *E. coli* (Goloubinoff et al., 1989a). In fact, *E. coli* GroEL-ES and Mg-ATP proved to be the only factors necessary for the reconstitution of a catalytically active *Rhodospirillum rubrum* Form II Rubisco (Goloubinoff et al., 1989b). However, only recently was Form I Rubisco assembled in vitro (Liu et al., 2010), which required both GroEL-ES and a small chaperone called RbcX (Larimer and Soper, 1993). RbcX appears to play a pivotal role in the solubility of LS and in vivo assembly of active holoenzyme in *Synechococcus* strains where the gene is located within the Rubisco operon (Onizuka et al., 2004; Emlyn-Jones et al., 2006; Saschenbrecker et al., 2007). In maize, the rbcX gene is expressed in leaves (Li et al., 2010), however the polypeptide remains to be detected in proteomic studies (Friso et al., 2010). Other than Cpn60, the only chloroplast protein shown to play a direct role in the folding or assembly of plant Rubisco is Bundle Sheath Defective 2 (BSD2), a DnaJ-like chaperone (Roth et al., 1996; Brutnell et al., 1999) with an unidentified mechanism of action.

Although plant and cyanobacterial Rubisco are both Form I, and the constituent proteins share over 80% amino acid identity (Parry et al., 2003), higher plant Rubisco has proven refractory to manipulation. When expressed in *E. coli*, higher plant SS and LS are insoluble, do not associate with one another to form oligomers, and no enzymatic activity is detectable (Gatenby et al., 1981; Gatenby, 1984; Gatenby et al., 1987; Parry et al., 2003). This implicates additional, and possibly plant-specific proteins, in higher plant Rubisco biogenesis.

SUMMARY OF THE INVENTION

In accordance with the present invention, modified higher plants are provided which comprise elevated levels of at least rubisco small subunit protein (SS) and ribulose-1,5-BisPhosphate Carboxylase/Oxygenase Accumulation Factor1 (RAF1) when compared to wild type plants. In an alternative embodiment, the plants of the invention comprise elevated levels of SS, RAF1 and LS. In a particularly preferred embodiment, the plants comprise elevated levels of SS, LS, RAF1 and BSD2 when compared to wild type. Surprisingly, the present inventors have discovered that plants comprising elevated levels of these proteins exhibit increased rubisco content and enhanced resistance to abiotic stress when compared to plants comprising levels found in untreated or wild type plants. In a preferred embodiment, the plant is maize and the abiotic stress is cold stress. In yet another preferred embodiment, the plants exhibit increased photosynthetic activity and increased biomass.

In another aspect of the invention, transgenic plants are provided which comprise heterologous nucleic acids encoding at least SS and RAF1, thereby producing plants harboring elevated levels of these proteins as compared to wild type. In another embodiment, the plants comprise heterologous nucleic acids encoding SS, RAF1 and LS. In yet another embodiment, the plants comprise heterologous nucleic acids encoding SS, RAF1, LS, and BSD2. These plants also exhibit increased cold resistance when compared to wild type plants lacking said heterologous nucleic acids. In certain embodiments, these plants also exhibit increased photosynthetic activity and increased biomass.

Also encompassed by the present invention are progeny, seeds and plant cells obtained from the modified or transgenic plants described herein.

BRIEF DESCRIPTION OF THE DRAWINGS

FIG. 2A: UBISS-LS$_N$; FIG. 2B: UBIBSD2; FIG. 2C: UBIRAF1; FIG. 2D: UBISS.

(FIG. 5B) LS abundance was quantified using the Odyssey scanner and normalized to the PSII protein D1 (n=7). Error bars represent the standard deviation; * P<0.0005.

DETAILED DESCRIPTION OF THE INVENTION

Figure 1:
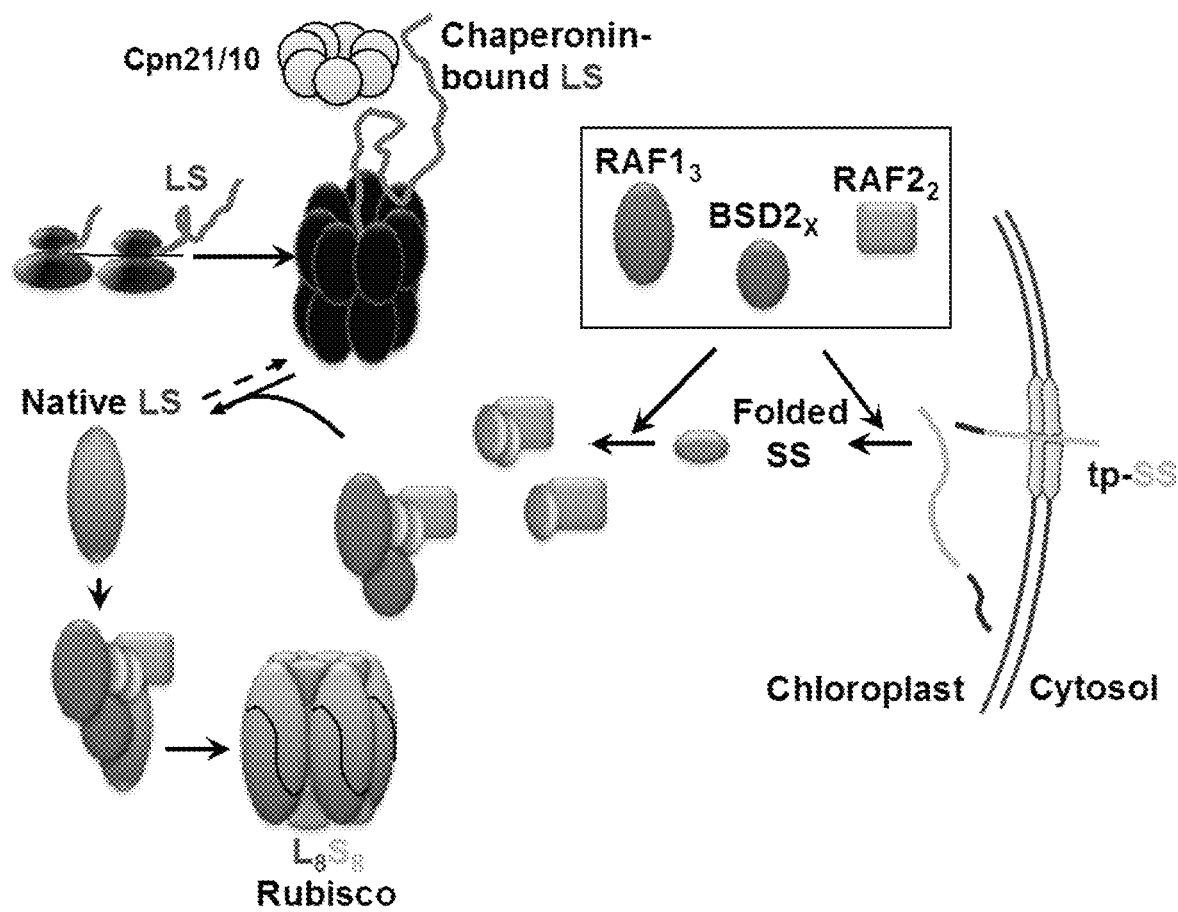
FIG. 1. Simplified model of the proteins required for Rubisco assembly in maize.
Figure 2A:
FIGS. 2A-2D show the constructs used to stably transform maize lines. Arrows represent the maize ubiquitin promoter. Verified lines were crossed in combinations to create stacked transgenic lines overexpressing different Rubisco subunits and assembly proteins. LSN denotes nucleus encoded LS.
Figure 2B:
Figure 2C:
Figure 2D:

Most life is ultimately sustained by photosynthesis and its rate limiting carbon fixing enzyme, Ribulose 1,5-bisphosphate carboxylase/oxygenase (Rubisco). This enzyme incorporates $CO_2$ into plant carbohydrates during photosynthesis. Atmospheric oxygen competes with $CO_2$ as a substrate for Rubisco, giving rise to photorespiration and making Rubisco the rate-limiting step in photosynthesis under certain conditions. Although the relatively simple cyanobacterial Rubisco is amenable to in vitro assembly, the hexadecameric higher plant enzyme has been refractory to such manipulation, due to poor understanding of its assembly pathway.

In accordance with the present invention, we created transgenic maize lines with enhanced Rubisco abundance. The data presented herein show that overexpression of Rubisco assembly factors and subunits will confer a physiological advantage to maize, specifically under cold stress conditions where Rubisco activity is limiting. Rubisco content has previously been increased 24-30% in transgenic rice, on a leaf area basis, through overexpression of endogenous SS (Suzuki et al. 2007) or a sorghum SS gene (Ishikawa et al. 2011). In both cases Rubisco activity was slightly decreased and the photosynthetic rate was not improved, even when Rubisco kcat was significantly increased. In maize, we previously overexpressed a nucleus-transplanted copy of the LS gene (LSN), and SS, both under control of the ubiquitin promoter (UBI-LS-SS). While both transgenes were expressed at a high level and nucleus-encoded LS was readily incorporated into holoenzyme, no overall change in Rubisco abundance was observed (Wostrikoff et al. 2012). Thus, in C3 rice increasing Rubisco abundance did not confer a photosynthetic advantage, and in C4 maize simply increasing subunit expression did not affect holoenzyme accumulation. From genetic analysis, we now know that apart from LS and SS, BSD2, RAF1, CPS2/Cpn60 and RAF2 are all required for Rubisco assembly and/or stability in maize. Taking advantage of this knowledge we have added ubiquitin promoter-driven expression of RAF1, or both BSD2 and RAF1 to the UBI-LS-SS line, which as shown below increases LS, and presumably holoenzyme abundance. Ubi-RAF2 transgenics can also be generated and can be introgressed into this background for a potential incremental increase above what we have observed.

The following definitions are provided to facilitate an understanding of the present invention.

As used herein, "genetically altered" means the modified expression of at least two, three or four of RAF1, a BSD2, LS, SS protein or both, or functional mutants thereof resulting from one or more genetic modifications; the modifications including but not limited to: recombinant gene technologies, induced mutations, and breeding stably genetically modified plants to produce progeny and seed comprising the altered gene product.

A "modified plant" is a plant that has been treated with an agent that increases expression of endogenous levels of at least SS/RAF1 when compared to wild type untreated plants. Alternatively the plant may be treated with an agent that elevates expression of SS/RAF1 and LS. In yet another embodiment, the treatment results in elevated levels of SS/RAF1/LS and BSD2.

A "transgenic plant" refers to a plant whose genome has been altered by the introduction of at least one heterologous nucleic acid molecule. Transgenic plants comprising altered RAF1 protein are provided herein.

The term "decreased" is intended to mean that the measurement of a parameter is changed by at least 10%, 20%, 30%, 40%, 50%, 60%, 70%, 80%, 90%, 100%, 200% or more when compared to the measurement of that parameter in a suitable control.

The term "increased" is intended to mean that the measurement of a parameter is changed by at least 10%, 20%, 30%, 40%, 50%, 60%, 70%, 80%, 90%, 100%, 200% or more when compared to the measurement of that parameter in a suitable control.

The terms "inhibit," "inhibition," "inhibiting", "reduced", "reduction" and the like as used herein refer to any decrease in the expression or function of a target gene product, including any relative decrement in expression or function up to and including complete abrogation of expression or function of the target gene product.

The terms "promote," "upregulate," "increase", and "overexpress", and the like as used herein refer to any increase in the expression or function of a target gene product, including any relative increase in expression or function of the target gene product.

The term "expression" as used herein in the context of a gene product refers to the biosynthesis of that gene product, including the transcription and/or translation of the gene product. Inhibition of expression or function of a target gene product (i.e., a gene product of interest) can be in the context of a comparison between any two plants, for example, expression or function of a target gene product (e.g., protein) in a genetically altered plant versus the expression or function of that target gene product in a corresponding wild-type plant. Expression levels can also be used to refer to increases or decreases in protein levels due to alterations in stability or assembly of such proteins. Inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription, translation, or stability or down-regulates functional activity of the target gene product can be used to achieve inhibition of expression or function of the target gene product.

The term "inhibitory sequence" encompasses any polynucleotide or polypeptide sequence that is capable of inhibiting the expression of a target gene product, for example, at the level of transcription or translation, or which is capable of inhibiting the function of a target gene product. Exemplary constructs encoding such inhibitory sequences are disclosed herein.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

Conversely, the terms "increase", "increased", and "increasing" in the context of the methods of the present invention refer to any increase in the expression or function of a gene product, including any relative increment in expression or function.

In many instances the nucleotide sequences for use in the methods of the present invention, are provided in transcriptional units for transcription in the plant of interest. A transcriptional unit is comprised generally of a promoter and a nucleotide sequence operably linked in the 3' direction of the promoter, optionally with a terminator.

"Operably linked" refers to the functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

Generally, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process, which includes the construction of a cDNA library from mRNA and isolation of distinct cDNA clones, yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA.

In one embodiment, the promoter element of the present invention precedes the 5' end of the recombinant nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the RAF1 and or BSD2 coding nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is readily measurable, e.g., by biological assay, immunoassay, radio immunoassay, or by colorimetric, fluorogenic, chemiluminescent or other methods. GFP is exemplified herein. The nucleic acid may be either RNA or DNA, linear or circular, single or double stranded, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional-termination signals and the like.

The term "selectable marker gene" refers to a gene that when expressed confers a selectable phenotype, such as herbicide tolerance, on a transformed plant cell.

The terms "recombinant plant," or "transgenic plant" refer to plants, which have a new combination of genes or nucleic acid molecules. A new combination of genes or nucleic acid molecules can be introduced into a plant using a wide array of nucleic acid manipulation techniques available to those skilled in the art.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins, with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp), which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

Preparation of SS, RAF1, LS, and BSD2 Encoding Nucleic Acid Molecules and Creation of Transgenic Plants Containing the Same Nucleic acid molecules of the invention encoding desired polypeptides may be prepared by two general methods: (1) synthesis from appropriate nucleotide triphosphates, or (2) isolation from biological sources. Both methods utilize protocols well known in the art.

The availability of nucleotide sequence information, such as the DNA sequences encoding LS, SS, RAF1 and/or BSD2, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

Specific probes/primers for identifying such sequences as the LS, SS, RAF1 or BSD2 encoding sequence may be between 15 and 40 nucleotides in length. For probes/primers longer than those described above, the additional contiguous nucleotides are provided the nucleic acid sequences in GenBank for these proteins.

Additionally, cDNA or genomic clones having homology with LS, SS, RAF1 and/or BSD2 may be isolated from other species using oligonucleotide probes corresponding to predetermined sequences within the target nucleic acids of the invention. Alternatively, the cDNA may be amplified by reverse transcriptase after making cDNA from the pool. The sequenced maize genome database provides the full length of cDNA and CDS. Such homologous sequences encoding the proteins of intereset may be identified by using hybridization and washing conditions of appropriate stringency. For example, hybridizations may be performed, according to the method of Sambrook et al., Molecular Cloning, Cold Spring Harbor Laboratory (1989), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes 1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows: $T_m 81.5° C. + 16.6$ Log $[Na+] + 0.41(\% G+C) - 0.63(\%$ formamide$) - 600/\#bp$ in duplex.

As an illustration of the above formula, using [Na+]= [0.368] and 50% formamide, with GC content of 42% and an average probe size of 200 bases, the $T_m$ is 57° C. The $T_m$ of a DNA duplex decreases by 11.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

Also encompassed within the scope of the invention are transgenic plants containing the aforementioned RAF1- and/or BSD2 encoding nucleic acids, or fragments or derivatives thereof.

The following example is provided to illustrate certain embodiments of the invention. It is not intended to limit the invention in any way.

Example I

Transgenic Plant Performance Under Chilling Temperatures

Due to the strong limitation Rubisco imposes on $CO_2$ assimilation at low temperatures, increasing Rubisco content may be a solution to enhance acclimation to cold in maize, as acclimation involving changes in Rubisco content does occur in some cool tolerant C4 species, such as Miscanthus (Dwyer et al. 2007, Sage and Kubien 2007). To our knowledge, this has never been directly been tested. We show that by overexpression of Rubisco produces high enough concentrations to avoid being limiting at low temperatures. The maize ubiquitin promoter was capable of overexpressing cold tolerance genes in rice under stress conditions (Ito et al. 2006), and should therefore be equally effective in maize grown at 14° C. Additionally, Rubisco activase, Cpn60, LS and SS maintain high average mRNA expression during chilling (Spence 2012). This suggests that decreases in Rubisco content in response to chilling occur post-transcriptionally or post-translationally, i.e. at the translational or protein stability level. Thus in principle, by increasing Rubisco content at least 40% we should be able to compensate for the ~40% decrease in Rubisco accumulation seen in maize under chilling temperatures.

Chloroplast-encoded LS interacts with the chaperonin complex to correctly fold the newly synthesized protein (Native LS). Nucleus-encoded SS is refolded after being translocated from the cytosol via the Tic-Toc complex. The data presented here show that several proteins, RAF2, RAF1 and/or BSD2 are involved in refolding imported SS, and also in forming assembly intermediates that capture folded LS once released from the chaperonin complex. In the absence of RAF2, RAF1 or BSD2, LS is subject to aggregation and proteolysis. Marginal holoenzyme assembly does occur in the absence of RAF2, thus it is possible that its role can be bypassed by RAF1 and BSD2. A schematic drawing of this complex is shown in FIG. 1.

Figure 3:
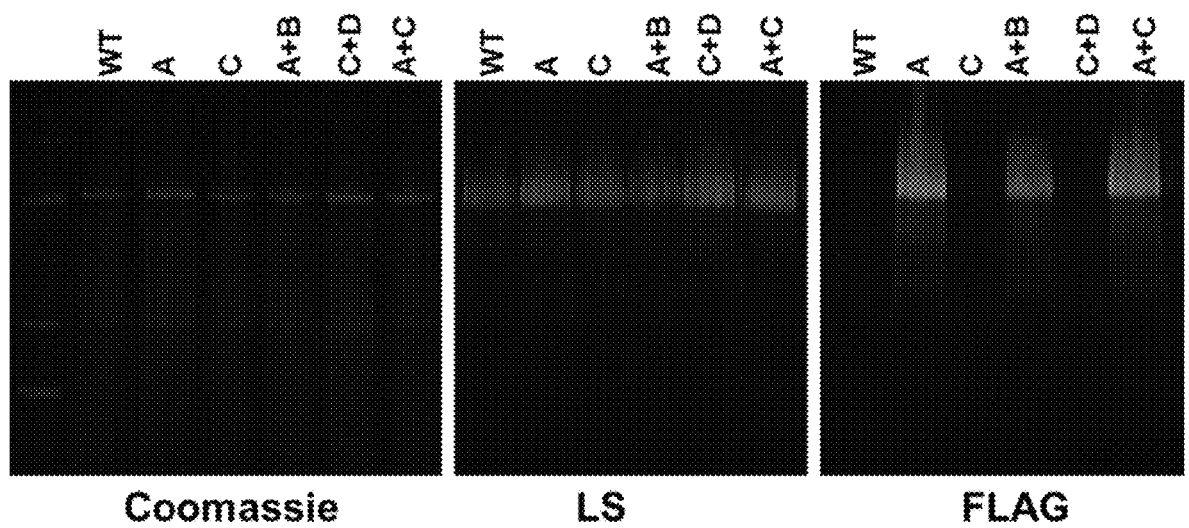
FIG. 3. Total protein extracted under native conditions on an equal leaf area basis and separated on native 4%-16% gradient acrylamide gels. Gels were stained with coomassie blue, or transferred to PVDF membrane and probed with anti-LS or anti-FLAG antibodies.
Figure 4:
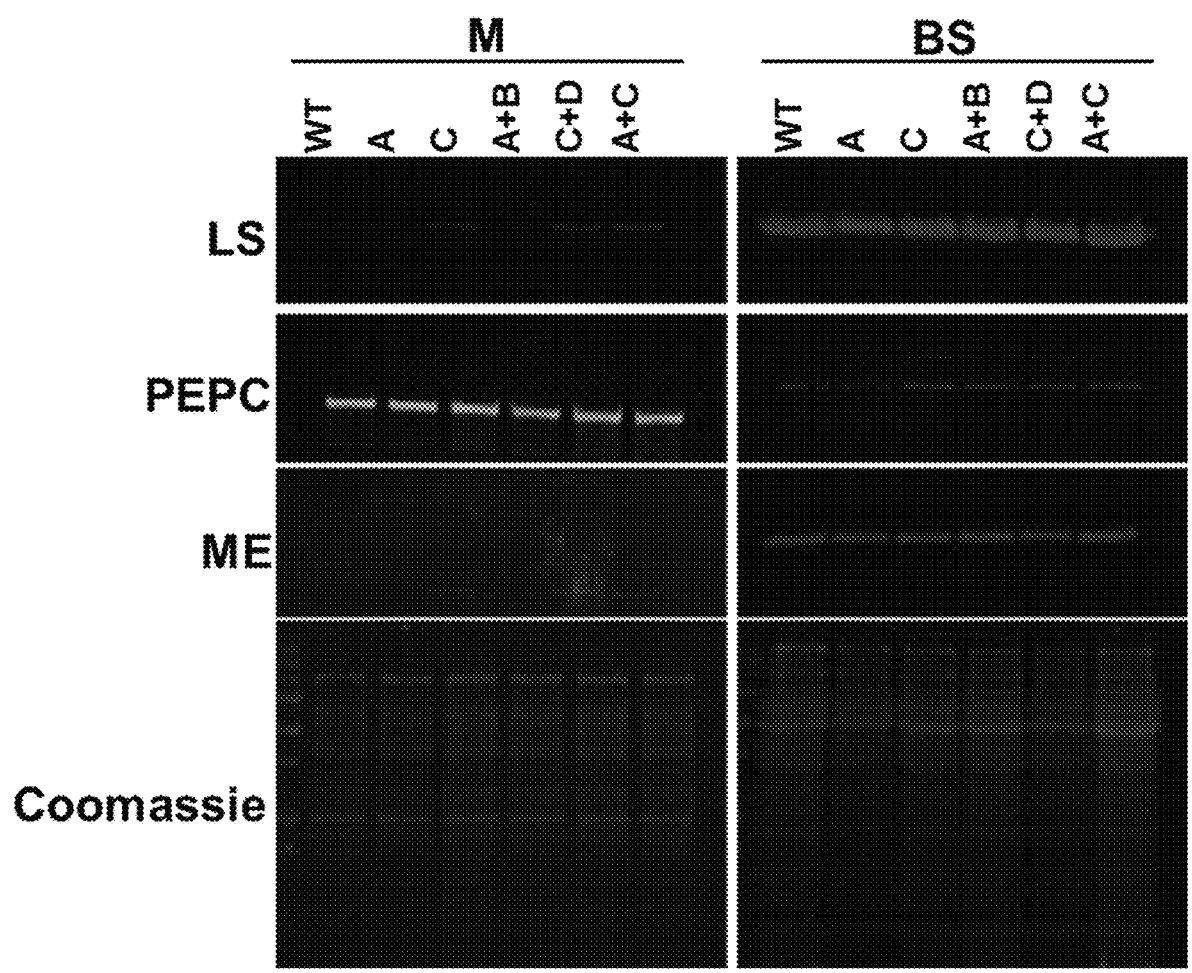
FIG. 4. Total proteins analyzed by immunoblot after Mesophyll (M) and Bundle Sheath (BS) cell isolation. A coomassie stained gel is present to reflect loading.

We employed a transgenic approach to highly express Rubisco subunits and assembly proteins. See FIG. 2 wherein combinations of constructs A+B, C+D, A+C, and A+B+C were created. The results shown in FIGS. 3 and 4 demonstrate that Rubisco is assembled as the holoenzyme in bundle sheath cells. Total rubisco migrated at 550 KD, indicating that Rubisco is soluble and assembled into the hexadecameric form. PEPC (present in M cells only) and ME (only present in BS cells) were used to evaluate cell separation purity. From this, LS appears to be accumulating only in BS cells.

Figure 5A:
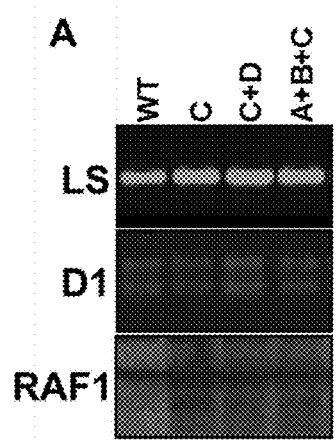
FIGS. 5A-5B (FIG. 5A) Total leaf soluble proteins were extracted on an equal leaf area basis and analyzed by immunoblot.
Figure 5B:
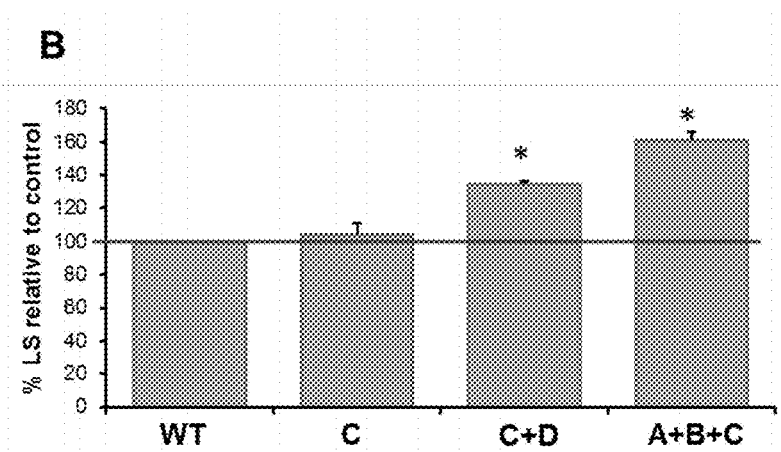
Figure 6:
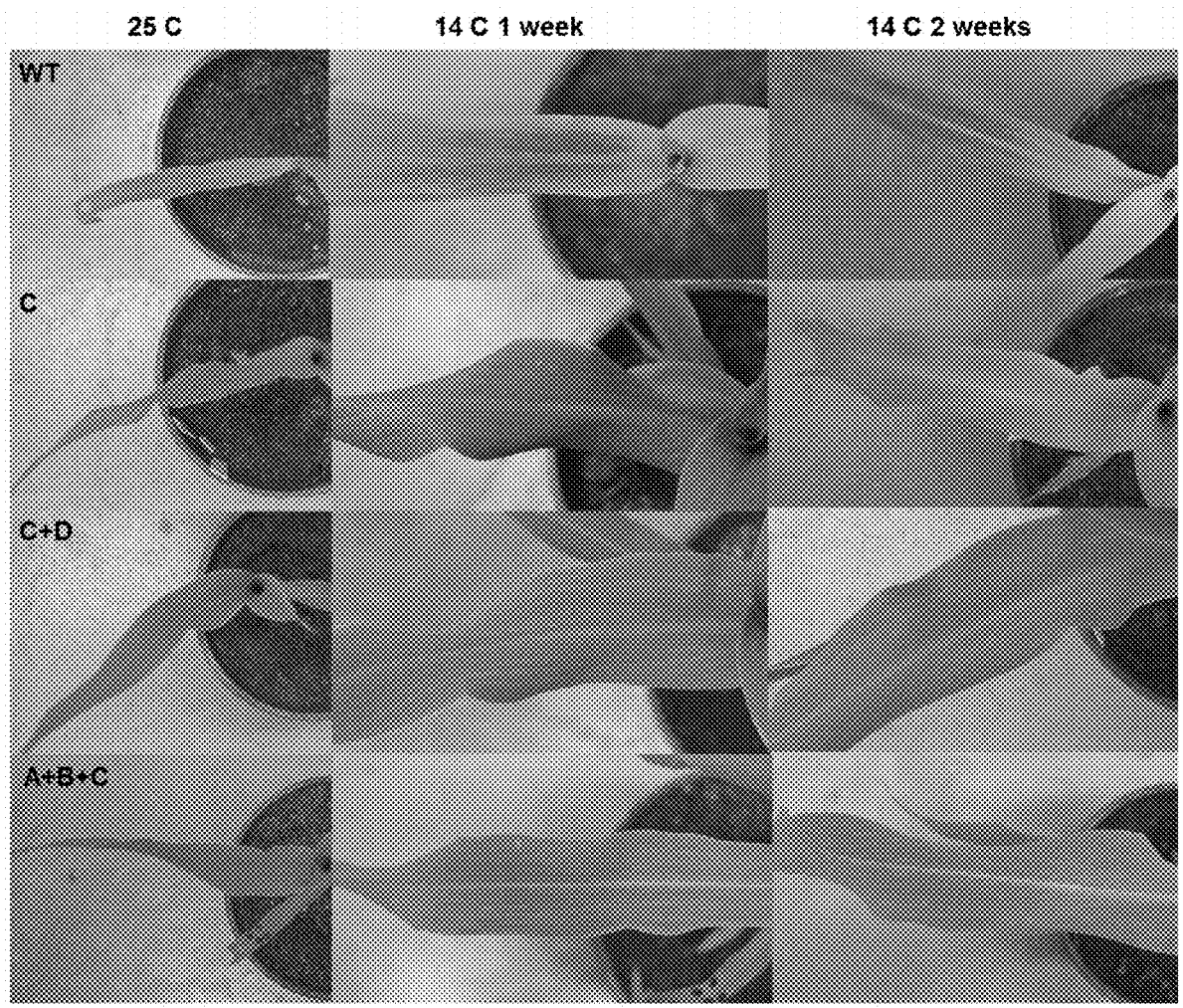
FIG. 6. Phenotype of transgenic maize leaves under cold stress. At day 18 after sowing we introduced chilling temperatures (14° C. day/12° C. night) for two weeks. Photograph shows maize leaves before and after plants were exposed to 14° C. days/12° C. nights for 0, 1 or 2 weeks.
Figure 7:
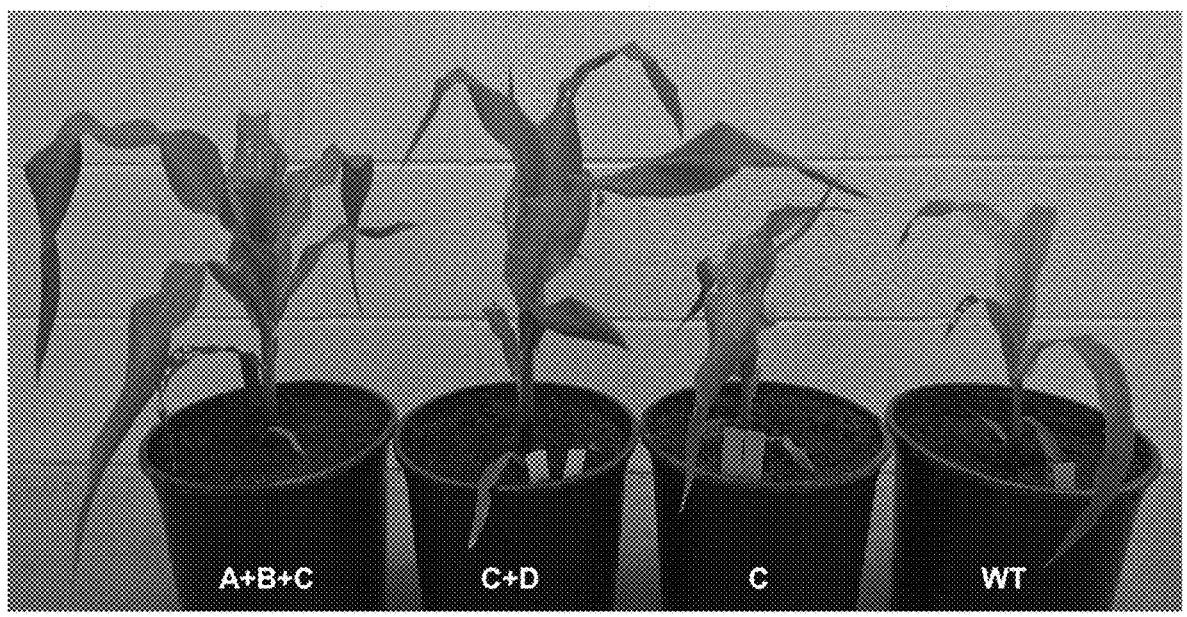
FIG. 7. Growth of transgenic maize plants under cold stress. Picture showing size difference between 32 day old plants containing different transgenes after 14 days in chilling conditions (14° C. days/12° C. nights).

To see if there was an obvious whole plant phenotype, we germinated UBI-RAF1, UBI-RAF1-SS, UBI-BSD2-LSN-SS-RAF1 and WT plants under 25° C. day/20° C. night conditions under high light (500 µmol photons m-2s-1). At day 18 after sowing we introduced chilling temperatures (14° C. day/12° C. night) for two weeks. 14° C. was used because maize has been shown to lose a significant proportion of its ability to assimilate $CO_2$ at and below that temperature (Naidu and Long 2004). We observed that a significant LS increase was found in the UBI-RAF1-SS (C+D) and the UBI-BSD2-LS$_N$-SS-RAF1 (A+B+C) lines (FIG. 5). FIG. 6 shows leaves before and after plants were exposed to 14° C. days/12° C. nights for 0, 1 or 2 weeks. The WT in this experiment was inbred B73, which is slightly less vigorous than the transgenic lines, which were created in the Hi-II hybrid background. Irrespective of size, the WT and UBI-RAF1 became increasingly chlorotic, whereas UBI-RAF1-SS and UBI-BSD2-LSN-SS-RAF1 largely maintained their chlorophyll content. At the end of the experiment (FIG. 7), WT and UBI-RAF1 plants appeared both chlorotic and stunted compared to the lines which had been found to harbor increased Rubisco at normal growth temperatures (FIG. 5). The comparison between UBI-RAF1 and UBI-RAF1-SS/UBIBSD2-LS$_N$-SS-RAF1 is particularly informative, because all are Hi-II derivatives propagated by selfing or outcrossing to other Hi-II lines, and their statures were similar at the outset of the experiment.

Figure 8:
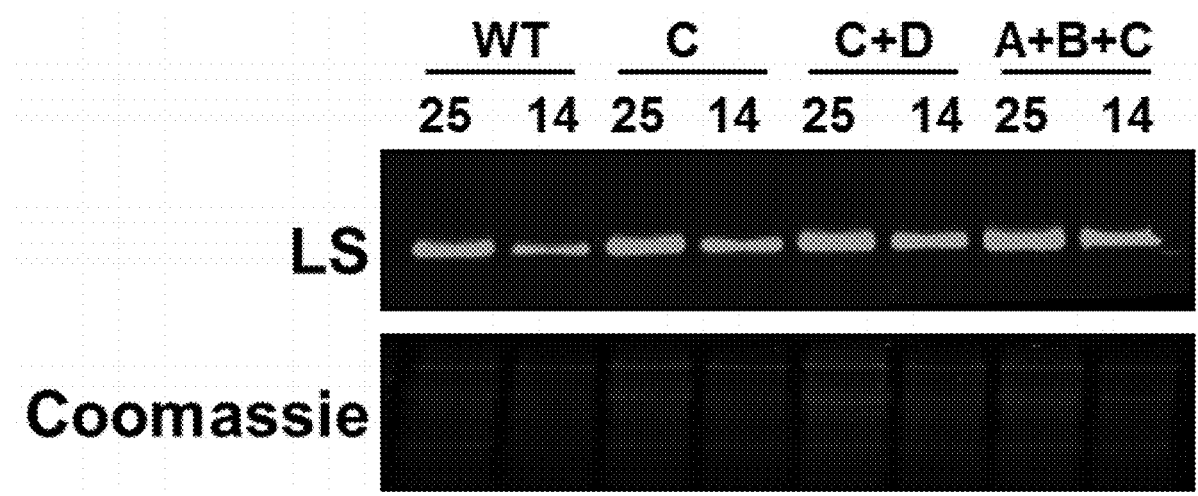
FIG. 8. Immunoblot analysis of LS before and after exposure to 14° C. day/12° C. night conditions for 2 weeks. Total leaf protein was extracted on an equal leaf area basis and samples were taken from the mid-point of the youngest fully expanded leaf (with leaf collar). Coomassie staining was included to reflect loading.

LS accumulation was measured in plants pre- and post cold stress, as shown in FIG. 8. We found that in the WT control, Rubisco decreased ~40% at chilling temperatures, in agreement with previous observations (Naidu et al. 2003, Spence 2012, Wang et al. 2008a). On the other hand, the decrease in Rubisco was mitigated in both UBI-RAF1-SS and UBI-BSD2-LS$_N$-SSRAF1 transgenic plants. Quantification of the gels in FIG. 8 indicates that these lines have comparable levels of Rubisco accumulation in the cold, to what WT plants possess at optimal growth temperatures. Thus, the apparent tolerance to chilling can be correlated with maintenance of sufficient Rubisco content. This correlation of high expression of Rubisco LS protein with maize tolerance to chilling temperatures provides an indication that the transgenic plants described are resistant to other abiotic stresses and provides the means to create such plants.

Figure 9:
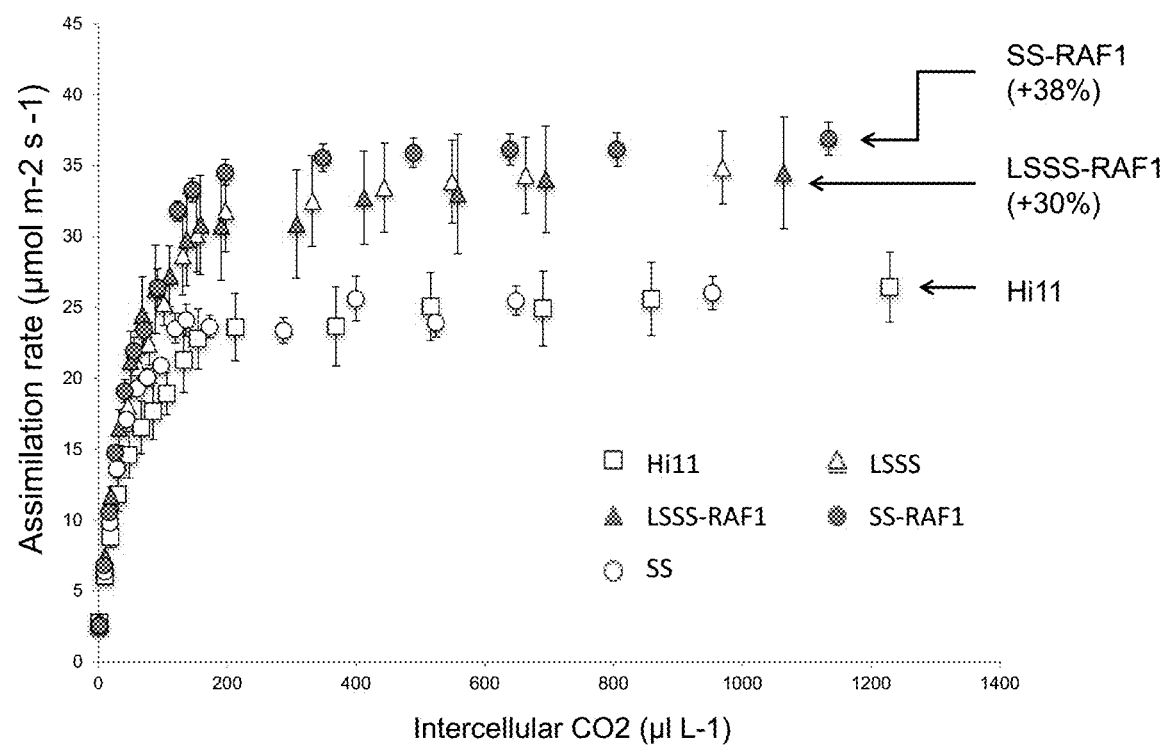
FIG. 9. A graph showing increased $CO_2$ assimilation in lines with higher Rubisco content at 14° C.
Figure 10:
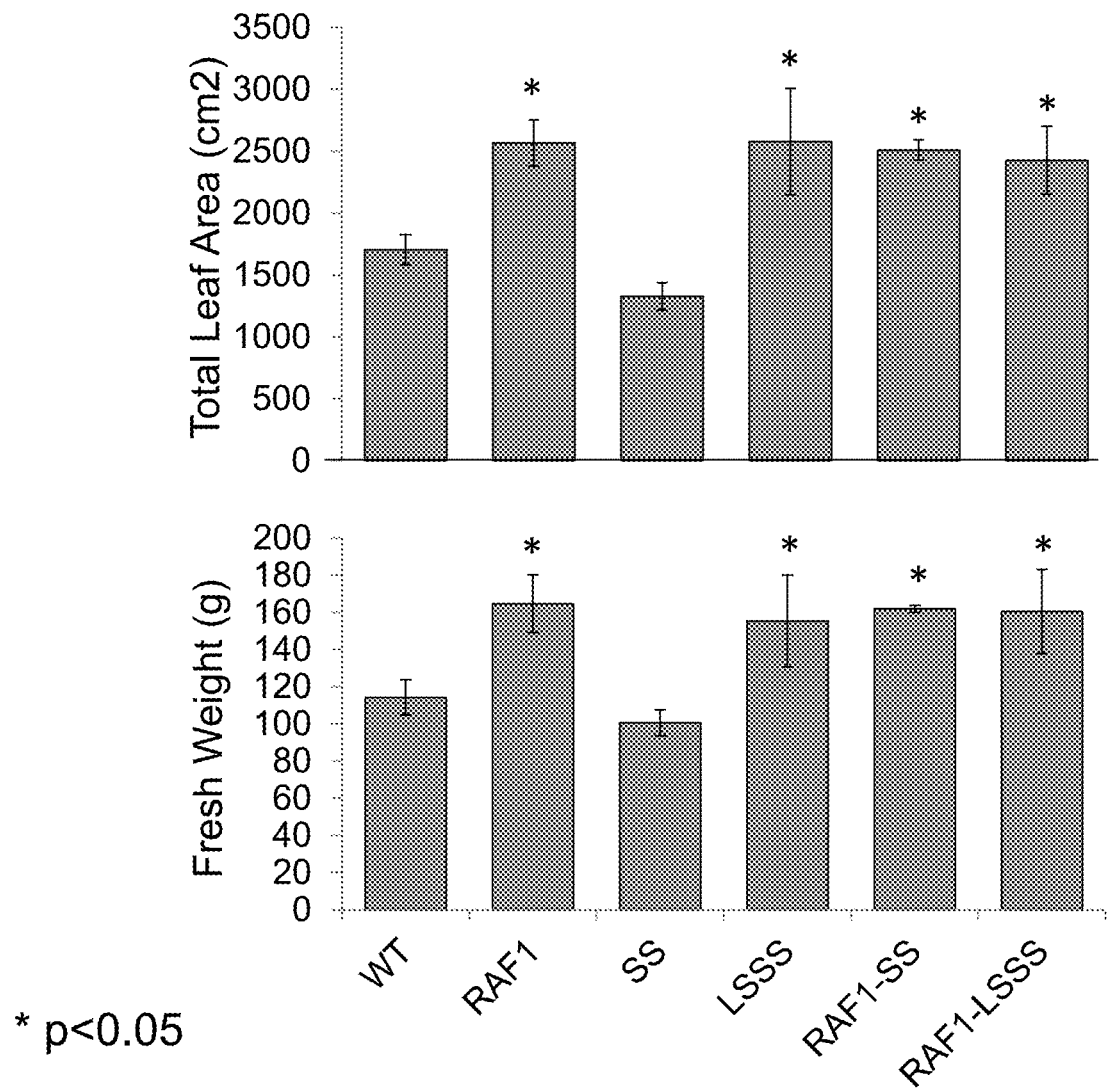
FIG. 10. A graph showing excess carbon fixed appears to be incorporated into biomass during chilling stress.

Gas exchange can be used to measures the rate of photosynthetic carbon assimilation. We performed additional studies to ascertain whether maintenance of rubisco content at low temperatures is important for sustaining photosynthetic capacity. FIG. 9 shows that the transgenic plants of the invention with higher rubisco content show increased $CO_2$ assimilation at 14° C. FIG. 10 shows that excess carbon fixed appears to be incorporated into biomass during chilling stress.

The results presented herein show that rubisco content can be increased by overexpression of the subunits and assembly factors and that the overexpressed rubisco was present as holoenzyme in bundle sheath chloroplasts. Increased Rubisco content correlates with much higher photosynthetic rates and increased biomass and leaf area under chilling conditions. Notably, increasing Rubisco appears to lessen the effects of chilling stress in higher plants, and in maize in particular.

REFERENCES (1) Long, S. P. (1983) *Plant Cell Environ.*, 6, 345-363.
(2) Wang, D., Portis, A. R., Jr., Moose, S. P. and Long, S. P. (2008) *Plant Physiol.*, 148, 557-567.
(3) Naidu, S. L. and Long, S. P. (2004) *Planta*, 220, 145-155.

(4) Naidu, S. L., Moose, S. P., AK, A. L.-S., Raines, C. A. and Long, S. P. (2003) *Plant Physiol.,* 132, 1688-169
(5) Spence, A. K. (2012) *Plant Biology.* Urbana, Illinois: Univ. Illinois Urbana-Champaign, pp. 146.
(6) Suzuki et al. (2007) *Plant Cell Physiol.,* 48:626-637.
(7) Whitney et al. (2015) *Proc Natl Acad Sci USA.* 112: 3564-3569.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A transgenic C4 plant comprising heterologous, recombinant nucleic acids for over-expressing rubisco small subunit (SS), rubisco large subunit (LS), and ribulose-1,5-Bis-Phosphate Carboxylase/Oxygenase Accumulation Factor1 (RAF1), over expression of said SS, LS and RAF1 increasing holoenzyme accumulation, said plant exhibiting increased rubisco content, increased photosynthetic rate, increased biomass and enhanced resistance to abiotic stress when compared to plants lacking said heterologous nucleic acids.

2. The transgenic plant of claim 1, which is a maize plant.

3. The transgenic plant of claim 1, further comprising a heterologous nucleic acid encoding bundle sheath defective 2 (BSD2).

4. The transgenic plant of claim 1, wherein said abiotic stress is cold stress.

5. The transgenic plant of claim 1, wherein said RAF1, SS and LS are operably linked to a ubiquitin promoter.

6. The transgenic plant of claim 1, wherein said RAF1, SS and LS heterologous, recombinant nucleic acids are from the same species of plant to be transformed.

* * * * *